United States Patent
Itagaki et al.

(10) Patent No.: US 6,388,160 B1
(45) Date of Patent: May 14, 2002

(54) METHOD FOR PRODUCING OF 2,3-DIMETHYLBUTENE-1 AND 2,3-DIMETHYLBUTENE-2

(75) Inventors: Makoto Itagaki, Takatsuki; Gohfu Suzukamo, Suita; Michio Yamamoto, Otsu, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/577,840

(22) Filed: May 25, 2000

(30) Foreign Application Priority Data

May 28, 1999 (JP) ............................. 11-149818

(51) Int. Cl.⁷ ............................. C07C 2/00; C07C 2/24; C07C 5/23
(52) U.S. Cl. ................ 585/512; 585/513; 585/329; 585/664
(58) Field of Search ................ 585/512, 513, 585/329, 664

(56) References Cited

U.S. PATENT DOCUMENTS

| | | | |
|---|---|---|---|
| 4,835,328 A | 5/1989 | Kent et al. ............... | 585/329 |
| 5,349,115 A | 9/1994 | Nomura et al. ........... | 585/513 |
| 5,910,618 A | 6/1999 | Nomura et al. ........... | 585/510 |

FOREIGN PATENT DOCUMENTS

| | | |
|---|---|---|
| CA | 2134982 | 9/1994 |
| EP | 0 231 748 A1 | 8/1987 |
| EP | 0 231 748 | 8/1987 |
| EP | 0 569 032 | 11/1993 |
| EP | 0 639 550 | 2/1995 |
| EP | 0 288 295 | 10/1998 |
| GB | 2 003 174 A | 3/1979 |
| JP | 47020104 A * | 9/1972 |
| JP | 09-110732 | 4/1997 |

OTHER PUBLICATIONS

Sato et al., "Studies on Nickel–Containing Ziegler–Type Catalysts. III. Dimerization of Propylene to 2,3–Dimethylbutenes, Part–I", *Bull. Chem. Soc. Jpn.*, vol. 66, 1993, pp. 3069–3078.

* cited by examiner

Primary Examiner—Walter D. Griffin
Assistant Examiner—Tam M. Nguyen
(74) Attorney, Agent, or Firm—Sughrue Mion, PLLC

(57) ABSTRACT

There is disclosed a method for producing 2,3-dimethylbutene-1 and 2,3-dimethylbutene-2, which is characterized by the steps of (a) dimerizing propylene in a propylene-dimerization step using a nickel complex catalyst as described below as a propylene-dimerization catalyst having propylene-dimerization activity and DMB-1 selectivity, (b) rectifying the resulting reaction solution to obtain 2,3-dimethylbutene-1 as a distillate and a distillation residue containing 2,3-dimethylbutene-1 in a 2,3-dimethylbutene-1 distillation step, (c) allowing the distillation residue to contact with sulfuric acid, sulfonic acid or hetetopolyacid to isomerize 2,3-dimethylbutene-1 in said distillation residue into 2,3-dimethylbutene-2 in an isomerization step, and (d) rectifying the resulting isomerization reaction solution to obtain 2,3-dimethylbutene-2 in a 2,3-dimethylbutene-2 distillation step, wherein said nickel complex catalyst containing (A) at least one nickel compound and the like, (B) a trialkylaluminum, (C) a trivalent phosphorus compound, (D) a fluorinated isopropanol or a halogenated phenol (E) at least one sulfur compound selected from a sulfonic acid and a dialkylsulfuric acid.

5 Claims, No Drawings

METHOD FOR PRODUCING OF 2,3-DIMETHYLBUTENE-1 AND 2,3-DIMETHYLBUTENE-2

BACKGROUND OF THE INVENTION

1. Field of the Invention

The present invention relates to a method for producing 2,3-dimethylbutene-1 and 2,3-dimethylbutene-2, which are useful intermediate for the production of agrochemicals, medicine, aromatics, cosmetics and the like.

2. Description of Related Art

There has been known a method for producing 2,3-dimethylbutene-1 (hereinafter, referred to as DMB-1) and 2,3-dimethylbutene-2 (hereinafter, referred to as DMB-2) as disclosed in Japanese Patent No. 2577772. Since it has been difficult, as the patent disclosed, to separate DMB-1 of good purity from propylene-dimerization reaction mixture containing a considerable amount of several by-products such as 4-methylpentene-1, cis or trans-4-methylpentene-2 of which boiling points differ from that of DMB-1 by only 1 to 3° C., DMB-1 has been produced by thermodynamically unfavorable reverse isomerization reaction of isolated DMB-2, which was prepared by isomerization DMB-1 contained in a propylene-dimerization reaction mixture.

SUMMARY OF THE INVENTION

An object of the invention is to provide an efficient method for production of DMB-1 and DMB-2, which has been accomplished by using a nickel catalyst having good selectivity and one isomerization step instead of cumbersome two isomerization steps including thermodynamically unfavorable reverse isomerization.

The present invention provides:

a method for producing 2,3-dimethylbutene-1 and 2,3-dimethylbutene-2, comprising the steps of (a) dimerizing propylene in a propylene-dimerization step using a nickel complex catalyst as described below as a propylene-dimerization catalyst having propylene-dimerization activity and DMB-1 selectivity, (b) rectifying the resulting reaction solution to obtain 2,3-dimethylbutene-1 as a distillate and a distillation residue containing 2,3-dimethylbutene-1 in a 2,3-dimethylbutene-1 distillation step, (c) allowing the distillation residue to contact with sulfuric acid, sulfonic acid or hetetopolyacid to isomerize 2,3-dimethylbutene-1 in said distillation residue into 2,3-dimethylbutene-2 in an isomerization step, and (d) rectifying the resulting isomerization reaction solution to obtain 2,3-dimethylbutene-2 in a 2,3-dimethylbutene-2 distillation step, wherein said nickel complex catalyst comprising (A) at least one nickel compound selected from a nickel salt of an organic or inorganic acid and a complex compound of nickel, (B) a trialkylaluminum, (C) a trivalent phosphorus compound of formula (1):

$$PR^1R^2R^3 \qquad (1)$$

wherein, $R^1$, $R^2$ and $R^3$ are the same or different and represent a phenyl which may be substituted with an alkyl or alkoxy group, an alkyl group, a cycloalkyl group or an aralkyl group, (D) a fluorinated isopropanol or a halogenated phenol of formula (2):

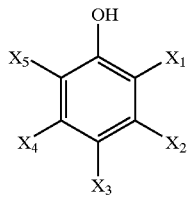

(2)

wherein $X_1$ to $X_5$ are the same or different and independently represent a halogen or hydrogen atom and at least one of $X_1$ to $X_5$ is a halogen atom, and (E) at least one sulfur compound selected from a sulfonic acid and a dialkylsulfuric acid.

DESCRIPTION OF THE PREFERRED EMBODIMENTS

The present invention will be described in detail below.

Examples of the nickel compound as the propylene-dimerization catalyst component (A) used in the present invention include an organic acid salt of nickel (e.g., (C1–C15) hydrocarbylcarboxylic acid such as nickel formate, nickel acetate and nickel naphthenate and the like), an inorganic acid salt of nickel such as nickel chloride, nickel bromide, nickel nitrate and the like, and a complex compound of nickel such as nickel bisacetyl acetonate and the like. These nickel compound can also be used in combination of two or more thereof.

Examples of the trialkylaluminum as the catalyst component (B) include tri(C1–C6) alkylaluminium such as trimethylaluminum, triethylaluminum, tri-n-propylaluminum, tri-n-butylaluminum, triisobutylaluminum, tri-n-pentylaluminum, tri-n-hexylaluminum and the like. The catalyst component (B) is used in an amount of usually about 2 to 500 moles, preferably about 2 to 100 moles per mol of the catalyst component (A).

Next, a description will be made to the trivalent phosphorus compound of formula (1).

Examples of the alkyl group on the phenyl group in $R^1$, $R^2$ or $R^3$ include a (C1–C3)alkyl group such as a methyl, ethyl, n-propyl, I-propyl group.

Examples of the alkoxy group on the phenyl group in $R^1$, $R^2$ and $R^3$ include a (C1–C3)alkoxy group such as a methoxy, ethoxy, n-propoxy or i-propoxy group.

Examples of the phenyl group which may be substituted with an alkyl or alkoxy group include a tolyl group, o-, m-, p-methoxyophenyl group.

Examples of the alkyl group for $R^1$, $R^2$ and $R^3$ include a (C1–C6) alkyl such as a methyl, ethyl, isopropyl, t-butyl, sec-butyl, n-pentyl or n-hexyl group.

Examples of the cycloalkyl group for $R^1$, $R^2$ and $R^3$ include a (C5–C6)cycloalkyl group such as a cyclopentyl or cyclohexyl group.

Examples of the aralkyl group include a (C7–C11)aralkyl group such as benzyl, phenylethyl, 1-, or 2-naphthylmethyl group.

Specific examples of the tri-valent phosphorus compound as the catalyst component (C) include triisopropylphosphine, tri-t-butylphosphine, tri-sec-butylphosphine, tricyclohexylphosphine, ethyl-di-t- butylphosphine, tri-o-tollylphosphine and the like. The catalyst component (C) is used in an amount of usually about 0.1 to 20 moles, preferably about 0.5 to 2 moles per mol of the catalyst component (A).

Examples of the fluorinated isopropanol as the catalyst component (D) include 1,1,3,3-tetrafluoroisopropanol, 1,1,1,3,3-pentafluoroisopropanol, 1,1,1,3,3,3-hexafluoroisopropanol and the like.

Examples of the halogenated phenols of formula (2) include o-, m-, p-chlorophenol, 2,3-, 2,4-, 2,6-, 3,4- and 3,5-dichlorophenol, 2,4,5- and 2,4,6-trichlorophenol, 2,3,4,6-tetrachlorophenol, pentachlorophenol and the like.

The amount of catalyst component (D) is usually about 0.4 to 20 moles, preferably about 1 to 10 moles per mol of the catalyst component (B).

Examples of the sulfonic acid selected as a sulfur compound as the catalyst component (E) include
an aliphatic sulfonic acid, (e.g., a (C1–C2)aliphatic sulfonic acid such as methanesulfonic acid, ethanesulfonic acid and the like),
an aromatic sulfonic acid such as benzenesulfonic acid, p-toluenesulfonic acid and the like having 6–7 carbon atoms, and
a halogen-containing sulfonic acid having up to 1 carbon atom such as chlorosulfonic acid, trifluoromethanesulfonic acid and the like.

Examples of the dialkylsulfuric acid include a di(C1–C2) alkylsulfuric acid such as dimethylsulfuric acid and diethylsulfuric acid. These can also be used in admixture of two or more thereof.

The amount of catalyst component (E) is usually about 0.1 to 10 moles per mol of the catalyst component (A).

The preparation of the catalyst is usually conducted in the presence of an inert solvent, and examples thereof include toluene, chlorobenzene, hexane, heptane, dichloroethane and the like. The mixing order of catalyst components is not particularly restricted, and the mixing of catalyst components is preferably conducted in the presence of a conjugated diene such as butadiene, isoprene and the like, and in this case, a catalyst having particularly good stability can be obtained. The conjugated diene is preferably used in an amount of about 1 to 200 moles per mol of the catalyst component (A).

The temperature for preparing the catalyst is usually from about −50 to 30° C. The propylene-dimerization reaction is conducted in an inert solvent such as toluene, chlorobenzene, hexane, heptane, dichloroethane. The concentration of the catalyst component in the reaction is usually from about $10^{-5}$ to $10^{-10}$ mol/l in terms of a nickel atom.

The reaction temperature is usually from about −20 to 50° C., the reaction time is usually from 30 minutes to 100 hours, and the pressures in the system is usually from 0 to 30 kg/cm²G.

Thus obtained propylene-dimerization reaction solution may be rectified as it is to obtain DMB-1, or the dimerization catalyst may be de-activated and removed before distillation of DMB-1. Examples of the de-activation agent for the propylene-dimerization include an aqueous solution such as ammonia water, an amine and the like, and aqueous de-activating agents such as an aqueous sodium hydroxide solution, aqueous potassium hydroxide solution and the like. When these aqueous de-activating agents are used, an aqueous layer is usually separated from an oil layer containing DMB-1, before distillation.

In the DMB-1 distillation step, DMB-1 having a purity of 92% or more can be obtained by rectification. DMB-1, which has a lower boiling point among the propylene-dimerization products, can be obtained as the initial fraction, and if necessary, 4-methylpentene-1, which has the lowest boiling point among the propylene-dimerization products, can be distilled off from the top of a column, then, desired DMB-1 can be obtained by distillation as DMB-1 pre-fraction.

The amount of DMB-1 to be distilled off from the top of a column can be optionally set. In other word, DMB-1 can be left in a bottom residue at the bottom of a column in an optional amount. Distillation is usually conducted, for example, so that the amount of DMB-1 to be distilled from the top of a column is 15% to 85% of the total amount of DMB-1 that is contained in the propylene-dimerization reaction solution.

The DMB-1 left in the residue may be recovered as a bottom product as it is. Alternatively it may be recovered as post-fraction DMB-1 from the top of a column by further distillation of the residue, while being separated from trimers or oligomers having higher boiling points.

The DMB-1 left in the residue or post fraction DMB-1 thus recovered can be isomerized into DMB-2 by using an isomerization catalyst.

Thus, the present method can be conducted by the following process sequence in which the distillation residue containing 2,3-dimethylbutene-1 obtained in step (b) is subjected to further distillation to give a post fraction containing 2,3-dimethylbutene-1, and allowing the post fraction to contact with sulfuric acid, sulfonic acid or heteropolyacid to isomerize 2,3-dimethylbutene-1 in said post fraction into 2,3-dimethylbutene-2, and rectifying the resulting isomerization reaction solution to obtain 2,3-dimethylbutene-2.

Examples of the isomerization catalyst include sulfuric acid,
an aliphatic sulfonic acid (e.g., (C1–C2)alkanesulfonic acid such as methanesulfonic acid, ethanesulfonic acid and the like);
a strong acidic ion exchange resin containing a sulfonic group,
a heteropolyacid such as silicotangstic acid, and the like.

The concentration of sulfuric acid to be used in usually 70% or more, preferably about 90 to 98%. The amount of sulfuric acid is usually from about 0.05 to 3 wt % based on the weight of DMB-1, depending on the concentration of the acid. The amount of the sulfonic acid is also usually from about 0.05 to 3 wt % based on DMB-1.

When a strong acidic ion exchange resin having a sulfonic group or heteropolyacid is used as the isomerization catalyst, DMB-1 can be isomerized into DMB-2 by a batch-wise method or continuous method in liquid phase or gas phase. When the isomerization reaction is conducted in a batch-wise method, a strong acidic ion exchange resin or heteropolyacid is used in an amount of about 0.1 to 1 wt % based on DMB-1. In the case of the continuous reaction, the isomerization reaction can be conducted by passing a mixture containing DMB-1 through a reaction tube filled with the catalyst, for example, at a space velocity of about 1 to 100/h$^{-1}$.

The isomerization reaction can be conducted without a solvent. An inert solvent like an aromatic hydrocarbon such as benzene, toluene and the like, an aliphatic hydrocarbon such as hexane, heptane and the like may be used in the reaction. The amount of the inert solvent, in case such a solvent is used, is usually about 0.01 to 10 parts by weight per 1 part by weight of DMB-1. A reaction solution that has been subjected to the isomerization reaction can also be used as a solvent in the isomerization reaction. The temperature of the isomerization reaction is usually from −30 to 100° C., preferably from 0 to 60° C.

When a sulfuric acid or a sulfonic acid is used as the isomerization catalyst, the acids may be removed after isomerization by adding an aqueous alkali solution to the reaction mixture to neutralize and separate them by phase separation.

When an ion exchange resin or heteropolyacid is used as the isomerization catalyst in a batch-wise method, the reaction mixture can be usually subjected to filtration to separate the catalyst before subsequent distillation, and when the isomerization is conducted by a continuous method, the reaction solution can be used as it is in the subsequent distillation.

DMB-2 having a purity of 99% or more can be obtained by distilling the isomerization reaction mixture containing DMB-2.

The present invention can provide an efficient method for simultaneous production of DMB-1 and DMB-2 in which a propylene dimerized reaction solution obtained by using a propylene-dimerization catalyst having good propylene-dimerizing activity and good DMB-1 selectivity is distilled to obtain DMB-1 of good purity, and further, the distillation residue containing DMB-1 is converted into a reaction solution containing DMB-2 by using an acid catalyst and the reaction solution is distilled to obtain DMB-2 of good purity.

EXAMPLES

The following examples further illustrate the present invention in detail below, but it is not to be construed to limit the scope of the invention thereto.

Example 1

Preparation of propylene-dimerization catalyst solution

A 50 ml schlenk tube was purged with nitrogen, then, cooled to 5° C., and to this were added, at this temperature, 1.35 ml of a toluene solution containing 0.1 mmol of nickel naphthenate, and 0.1 mmol of tricyclohexylphosphine and 8 mmol of isoprene, and further, a toluene solution containing 1.0 mmol of triethylaluminum. Then, 0.1 mmol of trifluoromethanesulfonic acid was added, then, 1.5 mmol of 1,1,1,3,3,3-hexafluoroisopropanol was added to obtain a propylene dimerization catalyst solution.

Example 2

Propylene-dimerization reaction

To a 1500 ml stainless autoclave purged with nitrogen were added the total amount of the above-described catalyst solution and 40 ml of toluene at 10° C., then, propylene was kept under 3 kg/cm$^2$G and fed to this, and the solution was reacted at 10° C. for 2 hours. The reaction solution was cooled to 5° C., then, the unreacted propylene was removed out of the system. The reaction mixture was analyzed by gas chromatography and the results are shown in Table 1 below.

TABLE 1

| | |
|---|---|
| Dimer selectivity | 74.5% |
| DMB-1 T.O.N. | 38210 |
| Dimer composition | |
| 4M1P | 2.0% |
| 4M2P | 4.0% |
| 2M1P | 9.6% |

TABLE 1-continued

| | |
|---|---|
| 2M2P | 2.2% |
| n-hexenes | 1.5% |
| DMB-1 | 78.4% |
| DMB-2 | 2.3% |

Note)
4M1P: 4-methylpentene-1, 4M2P: cis, trans-4-methlpentene-1, 2M1P: 2-methylpentene-1, 2M2P: 2-methylpentene-2, Dimer selectivity: (ratio of propylene-dimerization product to propylene reacted) × 100, DMB-1 T.O.N.: DMB-1 product (mmol)/amount of catalyst nickel (mmol)

Example 3

DMB-1 distillation

To the resulting propylene-dimerization reaction solution was added a 2% aqueous sodium hydroxide solution of about 1-fold by weight, and the solution was stirred for 1 hour at 40° C., then, after cooling the temperature to 20° C., separated to obtain 550 g of an oil layer.

550 g of the resulting reaction mixture (containing 320 g of DMB-1) was distilled at normal pressure using a 50-stage rectification column. In the distillation, whole reflux was initially conducted for 3 hours, then, 272 g of a fraction (54 to 56° C.) was drawn out from the top of the column at a reflux ratio of 30:1. The purity of this DMB-1 fraction was 94% (pre fraction DMB-1, DMB-1 recovering ratio: 80%). Further, the distillation residue was rectified at a reflux ratio of 30:1 to obtain 81 g of a 56 to 58° C. fraction.

The DMB-1 purity of this fraction was 75% (DMB-1 post fraction, DMB-1 recovering ratio: 19%).

Example 4

Isomerization of DMB-1 to DMB-2

To 80 g of the post fraction DMB-1 obtained in Examples 3 was added 0.4 wt % of 90% sulfuric acid, and the solution was reached for 3 hours at 30° C. Then, a 5% aqueous sodium hydroxide solution was added in an amount of 50 wt % to the reaction solution, and the solution was stirred for 0.5 hours at 25° C., then, separated to obtain 80 g of an oil layer. The reaction solution was analyzed by gas chromatography to show that the ratio of DMB-2 to DMB-1+DMB-2 was 91.0%, and DMB-2 contained therein was 52 g.

Example 5

A reaction tube (internal diameter: 7 mm, length: 15 cm) was filled with 2 ml of umberlist 15 (strong acidic ion exchange resin), then, 80 g of the post fraction DMB-1 (purity: 75%) obtained in the same manner as in Example 3 was passed through at 50° C. at a rate of 11.2 ml/hr for 8 hours. The amount of the resulted reaction solution was 67 g, and the ratio of DMB-2 to DMB-1+DMB-2 was 91.5%, and the DMB-2 content was 45.6 g.

Example 6

A reaction tube (internal diameter: 7 mm, length: 15 cm) was filled with 0.94 g (2 ml) of silicotungstic acid which had been supported on activated carbon and calcinated, then, 80 g of the post fraction DMB-1 (purity: 75%) obtained in the same manner as in Example 3 was passed through at 20° C. at a rate of 11.2 ml/hr for 8 hours. The amount of the resulting reaction solution was 67 g, and the ratio of DMB-2 to DMB-1+DMB-2 was 91.2%, and the DMB-2 content was 45.3 g.

Example 7

Distillation of DMB-2

80 g of the reaction solution obtained in Example 4 was distilled at normal pressure using a 30-stage rectification column. In the distillation, whole reflux was initially conducted for 2 hours, then, DMB-1, 4M2P, 2M1P, 2M2P were distilled off from the top of the column at a reflux ratio of 36:1, for removal thereof from the system (50 to 68° C. fraction). Then, the reflux ratio was lowered to 10:1, and 35 g of a 68 to 73° C. fraction was obtained. Gas chromatography analysis of this fraction showed that the purity of DMB-2 was 99.0%.

Example 8

The reaction was conducted in a similar manner according to Example 7 except that 67 g of the reaction solution obtained in Example 5 was used. The amount of the DMB-2 fraction was 30 g, and the purity of DMB-2 was 99.0%.

Example 9

The reaction was conducted in a similar manner according to Example 7 except that 67 g of the reaction solution obtained in Example 6 was used. The amount of the DMB-2 fraction was 30 g, and the purity of DMB-2 was 99.0%.

What is claimed is:

1. A method for producing 2,3-dimethylbutene-1 and 2,3-dimethylbutene-2, comprising the steps of
   (a) dimerizing propylene in a propylene-dimerization step using a nickel complex catalyst as described below as a propylene-dimerization catalyst having propylene-dimerization activity and 2,3 dimethylbutene-1 selectivity,
   (b) rectifying the resulting reaction solution to obtain 2,3-dimethylbutene-1 as a distillate and a distillation residue containing 2,3-dimethylbutene-1 in a 2,3-dimethylbutene-1 distillation step,
   (c) allowing the distillation residue to contact with sulfuric acid, sulfonic acid or hetetopolyacid to isomerize 2,3-dimethylbutene-1 in said distillation residue into 2,3-dimethylbutene-2 in an isomerization step, and
   (d) rectifying the resulting isomerization reaction solution to obtain 2,3-dimethylbutene-2 in a 2,3-dimethylbutene-2 distillation step, wherein said nickel complex catalyst comprising
   (A) at least one nickel compound selected from a nickel salt of an organic or inorganic acid and a complex compound of nickel,
   (B) a trialkylaluminum,
   (C) a trivalent phosphorus compound of formula (1):

$PR^1R^2R^3$ (1)

wherein, $R^1$, $R^2$ and $R^3$ are the same or different and independently represent a phenyl group which may be substituted with an alkyl or alkoxy group, an alkyl group, a cycloalkyl group or an aralkyl group,
   (D) a fluorinated isopropanol or a halogenated phenol of formula (2):

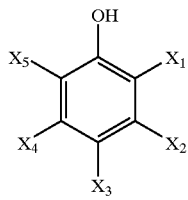

wherein $X_1$ to $X_5$ are the same or different and independently represent a halogen or hydrogen atom and at lease one of $X_1$ to $X_5$ is a halogen atom, and
   (E) at least one sulfur compound selected from a sulfonic acid and a dialkylsulfuric acid.

2. The method according to claim 1, wherein the sulfonic acid in the isomerization step is a strong acidic ion exchange resin having a sulfonic group.

3. The method according to claim 1 wherein the hetero-polyacid in the isomerization step is silicotungstic acid.

4. The method according to claim 1, 2 or 3 wherein the distillation residue containing 2,3-dimethylbutene-1 obtained in step (b) is subjected to further distillation to give a post fraction containing 2,3-dimethylbutent-1,
   (c) allowing the post fraction to contact with sulfuric acid, sulfonic acid or hetetopolyacid to isomerize 2,3-dimethylbutene-1 in said post fraction into 2,3-dimethylbutene-2, and
   (d) rectifying the resulting isomerization reaction solution to obtain 2,3-dimethylbutene-2.

5. The method according to claim 1, wherein the nickel complex catalyst comprises
   (A) at least one nickel compound selected from a nickel salt of a (C1–C15)hydrocarbylcarboxylic acid, nickel chloride, nickel bromide and nickel acetylacetonate,
   (B) a tri(C1–C6)alkylaluminum,
   (C) a trivalent phosphorus compound of formula (1):

$PR^1R^2R^3$ (1)

wherein, $R^1$, $R^2$ and $R^3$ are the same or different and independently represent a phenyl group which may be substituted with an (C1–C3)alkyl or (C1–C3)alkoxy group, an (C1–C6)alkyl group, a (C5–C6)cycloalkyl group or an (C7–C11)aralkyl group,
   (D) a fluorinated isopropanol or a halogenated phenol of formula (2) as defined in claim 1, and
   (E) at least one sulfur compound selected from a (C1–C2) aliphatic sulfonic acid, a (C6–C7)aromatic sulfonic acid, a halogen-containing sulfonic acid having up to 1 carbon atom and a di(C1–C2)alkylsulfuric acid.

* * * * *